United States Patent [19]

Sharma

[11] Patent Number: 5,683,679
[45] Date of Patent: Nov. 4, 1997

[54] ORAL COMPOSITIONS CONTAINING PEROXIDE WITH STABLE GREEN COLORANT

[75] Inventor: Vinay Sharma, Stratford, Conn.

[73] Assignee: Chesebrough-Pond's USA Co., Division of Conopco, Inc., Greenwich, Conn.

[21] Appl. No.: 570,989

[22] Filed: Dec. 12, 1995

[51] Int. Cl.$^6$ ............... A61K 7/16; A61K 7/20; A61K 33/40

[52] U.S. Cl. ............... 424/53; 424/49; 424/613; 424/616

[58] Field of Search ............... 424/49.08, 49.88, 424/613, 616

[56] References Cited

U.S. PATENT DOCUMENTS

| | | | |
|---|---|---|---|
| 3,747,232 | 7/1973 | Donaldson et al. | 35/26 |
| 4,022,880 | 5/1977 | Vinson et al. | |
| 4,077,911 | 3/1978 | Okumura et al. | 252/550 |
| 4,428,929 | 1/1984 | Wicheta et al. | 424/49 |
| 4,464,281 | 8/1984 | Rapisarda et al. | 252/99 |
| 4,476,108 | 10/1984 | Kessler et al. | 424/50 |
| 4,477,438 | 10/1984 | Willcockson | 424/130 |
| 4,684,517 | 8/1987 | Clipper et al. | 424/52 |
| 4,687,663 | 8/1987 | Schaeffer | |
| 4,803,008 | 2/1989 | Ciolino et al. | 252/162 |
| 4,822,854 | 4/1989 | Ciolino | 252/174.19 |
| 4,997,590 | 3/1991 | Bowling | 252/186.31 |
| 5,037,634 | 8/1991 | Williams et al. | |
| 5,085,853 | 2/1992 | Williams et al. | |
| 5,326,494 | 7/1994 | Woods | 252/186.27 |
| 5,392,947 | 2/1995 | Gentile | |
| 5,456,902 | 10/1995 | Williams et al. | |

*Primary Examiner*—Shep K. Rose
*Attorney, Agent, or Firm*—Milton L. Honig

[57] ABSTRACT

An oral composition is provided that includes a peroxide, a triphenylmethane class dye, a tartrazine class dye and a pharmaceutically acceptable carrier. Preferred embodiments of the dye system are FD&C Blue 1 and FD&C Yellow 5, in combination providing a green color. This green color is stable against degradation from the peroxide.

8 Claims, No Drawings

ORAL COMPOSITIONS CONTAINING PEROXIDE WITH STABLE GREEN COLORANT

BACKGROUND OF THE INVENTION

1. Field of the Invention

The invention relates to color stable peroxide compositions for use in the mouth.

2. The Related Art

Of recent there has been great commercial success in the marketing of peroxide products, especially baking soda and peroxide, for use in the oral cavity. A leading U.S. product in this field has been Mentadent® described in a series of patents including: U.S. Pat. No. 4,687,663; U.S. Pat. No. 5,037,634; U.S. Pat. No. 5,085,853; U.S. Pat. No. 5,392,947 and U.S. Pat. No. 5,456,902. Whether in liquid or semi-solid form, Mentadent® divides the baking soda and peroxide ingredients into two separated compositions. Ordinarily there is no color problem with the baking soda composition. However, the peroxide is highly reactive towards a whole range of colorants. Only FD&C Blue 1 has been found sufficiently safe and stable for commercial use.

Variants other than blue would be highly desirable. These non-blue systems are sought to distinguish various flavor variants from one another. The Colgate-Palmolive Company has been marketing a peroxide/baking soda dentifrice line, one of which includes a dual stripe of white and green. Their packaging indicates the colorants to be FD&C Blue 1 and FD&C Yellow 10. Stability may not be a serious problem in this product because the peroxide component is present at an extremely low level, as well as being encapsulated.

Older dental literature has reported other combinations of colorants for use in oral products. For instance, U.S. Pat. No. 4,022,880 (Vinson et al.) discloses in one of its examples an oral rinse combining FD&C Blue 1 with FD&C Yellow 5. Peroxides are not mentioned in conjunction with these colorants. Neither is there any disclosure with respect to color integrity problems.

Accordingly, it is an object of the present invention to provide a peroxide containing dentifrice or mouthwash with a colorant which does not fade through oxidative destruction.

It is another object of the present invention to provide a peroxide containing dentifrice or mouthwash composition with a green dye system of good color brightness which will not degrade in storage alongside the peroxide.

These and other objects of the present invention will become more readily apparent through consideration of the following summary and detailed description.

SUMMARY OF THE INVENTION

An oral composition is provided including:

(i) from 0.01 to 10% by weight of a peroxide compound;
(ii) from 0.00001 to 0.1% by weight of a triphenylmethane class dye;
(iii) from 0.00001 to 0.1% by weight of a tartrazine class dye; and
(iv) from 0.1 to 99.9% by weight of a pharmaceutically acceptable carrier.

DETAILED DESCRIPTION OF THE INVENTION

Now a highly stable green dye system has been discovered that does not fade in the presence of peroxides and which can be used in the oral cavity. This green dye system is a combination of a triphenylmethane class dye and tartrazine class dye. The most preferred embodiment is that of FD&C Blue 1 in combination with FD&C Yellow 5.

Thus, a first essential component of compositions according to the present invention is that of a peroxide compound. Typical examples include hydrogen peroxide, urea peroxide, calcium peroxide and the salts of perborate, persilicate, perphosphate and percarbonate. The most suitable for this invention is hydrogen peroxide. Amounts of the peroxide compound may range from 0.01 to 10%, preferably from 0.1 to 6%, optimally from 1 to 3% by weight.

A second essential component of compositions according to the present invention is that of a triphenylmethane class dye. Most preferred is FD&C Blue 1 having the structure (I):

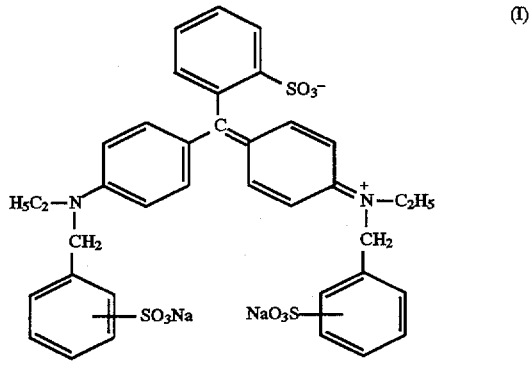

Amounts of this dye will range from 0.00001 to 0.1, preferably from 0.0001 to 0.005, optimally from 0.0005 to 0.001 by weight.

A third essential component of compositions according to the present invention is that of a tartrazine class dye. Most preferred is FD&C Yellow 5 having the structure (II):

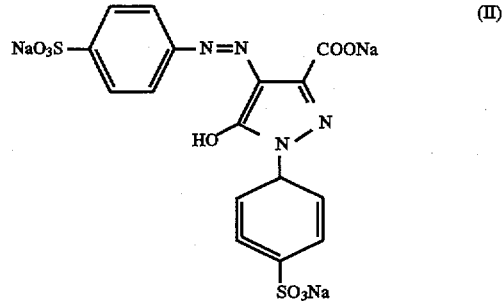

Amounts of this dye will range from 0.00001 to 0.1, preferably from 0.0001 to 0.005, optimally from 0.0005 to 0.001 by weight.

In accordance with the preferred embodiment, the relative weight ratios of FD&C Blue 1 and FD&C Yellow 5 may range from 3:1 to 1:3, preferably from 2:1 to 1:2, more preferably from 1.5:1 to 1:1.5, optimally about 1:1.

Oral compositions of the present invention may be in the form of either a dentifrice (e.g. paste or gel) or mouthwash.

A fourth essential component of compositions according to the present invention is that of a pharmaceutically acceptable carrier. The term "pharmaceutically acceptable carrier" will include such functional ingredients as water, humectants, abrasives, thickeners and surfactants. Total levels of these materials may range anywhere from 0.1 to 99.9%, preferably from 20 to 99% by weight.

Water may be present in the compositions in amounts ranging from about 20 to about 99% by weight. When the peroxide composition is a gel, the amount of water may range from about 30 to about 55%, optimally between 35 and 45% by weight.

Humectants are usually polyols which, for example, may include glycerol, sorbitol, propylene glycol, lactitol, xylitol, polypropylene glycol, polyethylene glycol, hydrogenated corn syrup and mixtures thereof. Generally the amount of humectant will range from 25 to 90%, preferably from 40 to 70% by weight.

Where the oral compositions are mouthwashes, it is often desirable to include ethanol as a carrier. Levels of ethanol may range from 0.5 to 40%, preferably from 1 to 30%, optimally from 5 to 25% by weight.

A natural or synthetic thickening agent may be present in an amount from about 0.1 to about 10%, preferably about 0.5 to 5% by weight. Thickeners may include hydroxypropyl methylcellulose, hydroxyethyl cellulose, sodium carboxymethyl cellulose, xanthan gum, tragacanth gum, karaya gum, arabic gum, Irish moss, starch, alginates and carrageenans.

When the compositions are in the form of a gel, it may be desirable to utilize a thickening agent that is a combination of water and a crosslinked acrylic polymer and/or a polyoxyethylene/polyoxypropylene copolymer. Most preferred is the polyoxyethylene/polyoxypropylene copolymer, especially one having a hydrophobic portion, represented by $(C_3H_6O)$, with a molecular weight range from about 2,750 to 4,000 and a hydrophilic portion, represented by $(C_2H_4O)$, constituting about 70–80% of the weight of the copolymer.

Commercially, the above mentioned copolymers are available from the BASF Corporation under the trademark, Pluronic F88, F99, F108 and F127. Most preferred is Pluronic F127 (more commonly described by its CTFA name, Poloxamer 407) which has a molecular weight ranging from about 10,000 to 15,000, and containing about 70% of the hydrophilic polyoxyethylene moiety. Amounts of the copolymer can range anywhere from 18–25% by weight, preferably between 19 and 24%. Poloxamers are particularly suitable for this invention because of their wide pH tolerance, high compatibility with hydrogen peroxide and unique gel properties.

When in the form of a dentifrice, a carrier may include an abrasive. Illustrative abrasives are sodium bicarbonate, silicas, aluminas, calcium carbonate and salts of metaphosphate. Especially preferred are sodium bicarbonate and silica. Amounts of the abrasive may range from 5 to 80% by weight.

Surfactants may also be a constituent of the pharmaceutically acceptable carrier. The surfactant may be of the anionic, nonionic, cationic or amphoteric type. Most preferred are sodium lauryl sulphate, sodium dodecylbenzene sulphonate and sodium laurylsarcosinate. Surfactants are usually present in amounts from 0.5 to 10%, preferably from 1 to 5% by weight.

Tartar control agents may be incorporated into compositions of this invention, especially effective will be agents containing phosphorous. Inorganic phosphorous tartar control agents may include any of the pyrophosphates such as disodium pyrophosphate, dipotassium pyrophosphate tetrapotassium pyrophosphates, tetrasodium pyrophosphates and mixtures thereof. Organic phosphorous compounds that may serve as tartar control agents include polyphosphonates such as disodium ethane-1-hydroxy-1, 1-diphosphonate (EHDP), methanediphosphonic acid, and 2-phosphonobutane-1,2,4-tricarboxylic acid.

For anti-caries protection, a source of fluoride ion will normally be present. Fluoride sources include sodium fluoride, potassium fluoride, calcium fluoride, stannous fluoride, stannous monofluorophosphate and sodium monofluorophosphate. These sources should release anywhere from 25 to 3500 ppm of fluoride ion. The anti-caries agent will be present in an amount from about 0.05 to about 3%, preferably 0.2 to 1% by weight of the composition.

Sweetening agents such as saccharin, sodium cyclamate, aspartame, sucrose and the like may be included at levels from about 0.1 to 5% by weight.

Other additives may also be incorporated into the oral compositions including preservatives, silicones, other synthetic or natural polymers such as Gantrez S-97, and anti-gingivitis actives.

Colored peroxide compositions of this invention may be used in combination with a second alkaline composition such as one containing 0.1–80% baking soda. A preferred embodiment will place the peroxide and alkaline compositions in separate compartments of a dual-chamber dispenser. Only upon dispensing will portions of each composition mix. An advantage of the green colorant system according to this invention is that the green color will remain stable even in contact with the alkaline (pH 7–11) composition.

The following examples will more fully illustrate the embodiments of this invention. All parts, percentages and proportions referred to herein and in the appended claims are by weight of the total composition unless otherwise stated.

EXAMPLE 1

A mouthwash according to the present invention was prepared with the formulation as described under Table I.

TABLE II

| COMPONENT | WEIGHT % |
|---|---|
| Ethanol (190 Proof) | 10.4 |
| Hydrogen Peroxide (35% Solution) | 4.3 |
| Pluronic ® F127 | 1.0 |
| Flavor | 0.2 |
| Methylsalicylate | 0.08 |
| Phosphoric Acid (85% Solution) | 0.042 |
| FD&C Blue 1 | 0.0014 |
| FD&C Yellow 5 | 0.0019 |
| Water | balance |

EXAMPLE 2

Comparative stability studies were performed on the compositions listed under Table II.

TABLE II

| | FORMULA NO. (WEIGHT %) | |
|---|---|---|
| COMPONENT | 1 | 2 |
| Ethanol (190 Proof) | 10.4 | 10.4 |
| Hydrogen Peroxide (35% Solution) | 4.3 | 4.3 |
| Pluronic ® F127 | 1.0 | 1.0 |
| Flavor | 0.2 | 0.2 |
| Methylsalicylate | 0.08 | 0.08 |
| Phosphoric Acid (85% Solution) | 0.04 | 0.04 |
| FD&C Blue 1 | 0.0007 | 0.0007 |
| FD&C Yellow 5 | 0.00095 | — |
| FD&C Yellow 10 | — | 0.00095 |
| Water | balance | balance |

Long term color stability of formulas 1 and 2 was evaluated spectrophotometrically by scanning the maximum color absorption peak of 410 and 631 nm. Samples of each of the formulas were monitored for a three month period, under room temperature storage conditions. Other samples were subjected to accelerated aging by heating at a temperature of 95° C. over a 6 hour period. Results are reported in Table III.

TABLE III

COLOR STABILITY AFTER STORAGE

FORMULA 1

| STORAGE CONDITION | ABSORPTION AT 631 NM (BLUE 1) | % BLUE 1 REMAINING | ABSORPTION AT 410 NM (YELLOW 5) | % YELLOW 5 REMAINING |
| --- | --- | --- | --- | --- |
| Initial @ 25° C. | 1.99 | — | 1.00 | — |
| 6 hours @ 95° C. | 1.85 | 93% | 1.00 | 100% |
| 24 hours @ 95° C. | 1.31 | 67% | 0.65 | 65% |
| 3 weeks @ 25° C. | 2.00 | 100% | 1.00 | 100% |
| 3 months @ 25° C. | 2.00 | 100% | 1.00 | 100% |

FORMULA 2

| STORAGE CONDITION | ABSORPTION AT 631 NM (BLUE 1) | % BLUE 1 REMAINING | ABSORPTION AT 410 NM (YELLOW 10) | % YELLOW 10 REMAINING |
| --- | --- | --- | --- | --- |
| Initial @ 25° C. | 1.93 | — | 2.05 | — |
| 6 hours @ 95° C. | 1.24 | 65% | 1.24 | 64% |
| 3 weeks @ 25° C. | | - visually pale green - | | |

Formula 1 with a combination of FD&C Blue 1 and Yellow 5 exhibited very little color loss even after three months at 25° C. Accelerated aging at 95° C. for six hours also had no adverse influence on the color stability. By contrast, Formula 2 incorporating FD&C Blue 1 and Yellow 10 was degraded after only three weeks at 25° C. to an extent even visible to the naked eye, i.e. a pale green. Accelerated storage conditions of six hours at 95° C. reduced the active dyes down to a level of about 65%.

EXAMPLE 3

A toothpaste according to the present invention may be prepared with the formulation as described under Table IV.

TABLE IV

| COMPONENT | WEIGHT % |
| --- | --- |
| Glycerin | 20.0 |
| Hydrated Silica | 20.0 |
| Propylene Glycol | 20.0 |
| Sodium Bicarbonate | 20.0 |
| Sodium Carbonate | 5.0 |
| Tetrasodium Pyrophosphate | 3.0 |
| Pentasodium Triphosphate | 2.0 |
| PEG-12 | 2.0 |
| Sodium Lauryl Sulfate | 1.5 |
| Calcium Peroxide | 1.0 |
| Flavor | 1.0 |
| Sodium Saccharin | 0.8 |
| Cellulose Gum | 0.4 |
| Sodium Monofluorophosphate | 0.3 |
| Titanium Dioxide | 0.3 |
| Xanthan Gum | 0.3 |
| FD&C Blue 1 | 0.002 |
| FD&C Yellow 5 | 0.002 |
| Water | balance |

EXAMPLE 4

Another example of a dentifrice according to the present invention may be prepared with the formulation as described under Table V.

TABLE V

| COMPONENT | WEIGHT % |
| --- | --- |
| Sodium Bicarbonate | 34.0 |
| Polyethylene Glycol | 32.0 |
| Sodium Percarbonate | 4.0 |
| Silica (Aerosil 200) | 2.0 |
| Sodium Acetate | 1.0 |
| Saccharin | 0.9 |
| Flavor | 0.75 |
| Sodium Lauroyl Sarcosinate | 0.5 |
| Sodium Fluoride | 0.24 |
| FD&C Blue 1 | 0.002 |
| FD&C Yellow 5 | 0.002 |
| Water | balance |

EXAMPLE 5

An example of a gel type dentifrice according to the present invention may be prepared with the formulation as described under Table VI.

TABLE VI

| COMPONENT | WEIGHT % |
| --- | --- |
| Glycerin | 40.0 |
| Pluronic ® F127 | 20.0 |
| Hydrogen Peroxide (35% Active) | 4.285 |
| Phosphoric Acid | 0.15 |
| FD&C Blue 1 | 0.0014 |
| FD&C Yellow 5 | 0.0019 |
| Water | balance |

The foregoing description and examples illustrate selected embodiments of the present invention. In light thereof, various modifications will be suggested to one skilled in the art, all of which are within the spirit and purview of this invention.

What is claimed is:

1. An oral composition comprising:

(i) from 0.01 to 10% by weight of a peroxide compound;

(ii) from 0.00001 to 0.1% by weight of a triphenylmethane class dye which is FD&C Blue 1;

(iii) from 0.00001 to 0.1% by weight of a tartrazine class dye which is FD&C Yellow 5, the triphenylmethane and tartrazine dyes being in an amount sufficient to provide a green color to the composition having good color brightness which will not degrade in storage alongside the peroxide compound; and (iv) from 0.1 to 99.9% by weight of a pharmaceutically acceptable carrier.

2. The composition according to claim 1, wherein the triphenylmethane class dye and tartrazine class dye are present in respective weight ratios of 3:1 to 1:3.

3. The composition according to claim 1, wherein the triphenylmethane class dye and tartrazine class dye are present in respective weight ratios of 2:1 to 1:2.

4. The composition according to claim 1 further comprising from 0.5 to 40% by weight of ethanol.

5. The composition according to claim 1 wherein the peroxide compound is selected from the group consisting of hydrogen peroxide, urea peroxide, calcium peroxide, persilicate, perphosphate, persulphate, perborate and percarbonate.

6. A composition according to claim 1 wherein the peroxide compound is hydrogen peroxide.

7. The composition according to claim 1 within the peroxide compound is calcium peroxide.

8. The composition according to claim 1 wherein the peroxide compound is sodium percarbonate.

* * * * *